United States Patent [19]

Furuta et al.

[11] Patent Number: 4,612,289

[45] Date of Patent: Sep. 16, 1986

[54] METHOD FOR ANALYZING LIQUID SAMPLE

[75] Inventors: Yoshiteru Furuta, Katsuta; Yasushi Nomura, Mito, both of Japan

[73] Assignee: Hitachi, Ltd., Tokyo, Japan

[21] Appl. No.: 319,033

[22] Filed: Nov. 6, 1981

[30] Foreign Application Priority Data

Nov. 10, 1980 [JP] Japan .................................. 55-158665

[51] Int. Cl.[4] ....................... G01N 21/78; G01N 33/50
[52] U.S. Cl. ..................................... 436/34; 435/805; 436/45; 436/50; 436/164; 422/64
[58] Field of Search ................... 436/43, 46, 47, 50, 436/51, 164, 172, 34, 45; 422/64, 65, 67; 356/432, 433, 434, 436; 435/805

[56] References Cited

U.S. PATENT DOCUMENTS

| | | | |
|---|---|---|---|
| 3,701,601 | 10/1972 | Plumpe, Jr. et al. | 356/436 |
| 3,847,486 | 11/1974 | McCabe | 356/434 |
| 3,963,909 | 6/1976 | Atwood et al. | 436/34 |
| 4,276,051 | 6/1981 | Ginsberg et al. | 436/47 |
| 4,311,394 | 1/1982 | Manabe | 356/434 |
| 4,313,735 | 2/1982 | Yamashita et al. | 436/47 |
| 4,472,505 | 9/1984 | Manabe et al. | 436/47 |

*Primary Examiner*—Arnold Turk
*Attorney, Agent, or Firm*—Antonelli, Terry & Wands

[57] ABSTRACT

In analysis of a liquid sample by adding a reagent to a liquid sample, thereby initiating reaction, and measuring a rate of the reaction, thereby quantitatively determining an analytical item being contained in the sample and taking part in the reaction, the analysis is carried out by measuring a physical quantity of the liquid sample, setting an effective limit level for the sample, then adding a reagent to the sample, measuring a physical quantity of the resulting liquid mixture, and computing the analysis value of the desired analytical value of the sample from the physical quantities so far measured before the effective limit level is reached. An exact effective limit level can be automatically set for the individual sample, and thus an analysis value can be obtained with high exactness.

9 Claims, 4 Drawing Figures

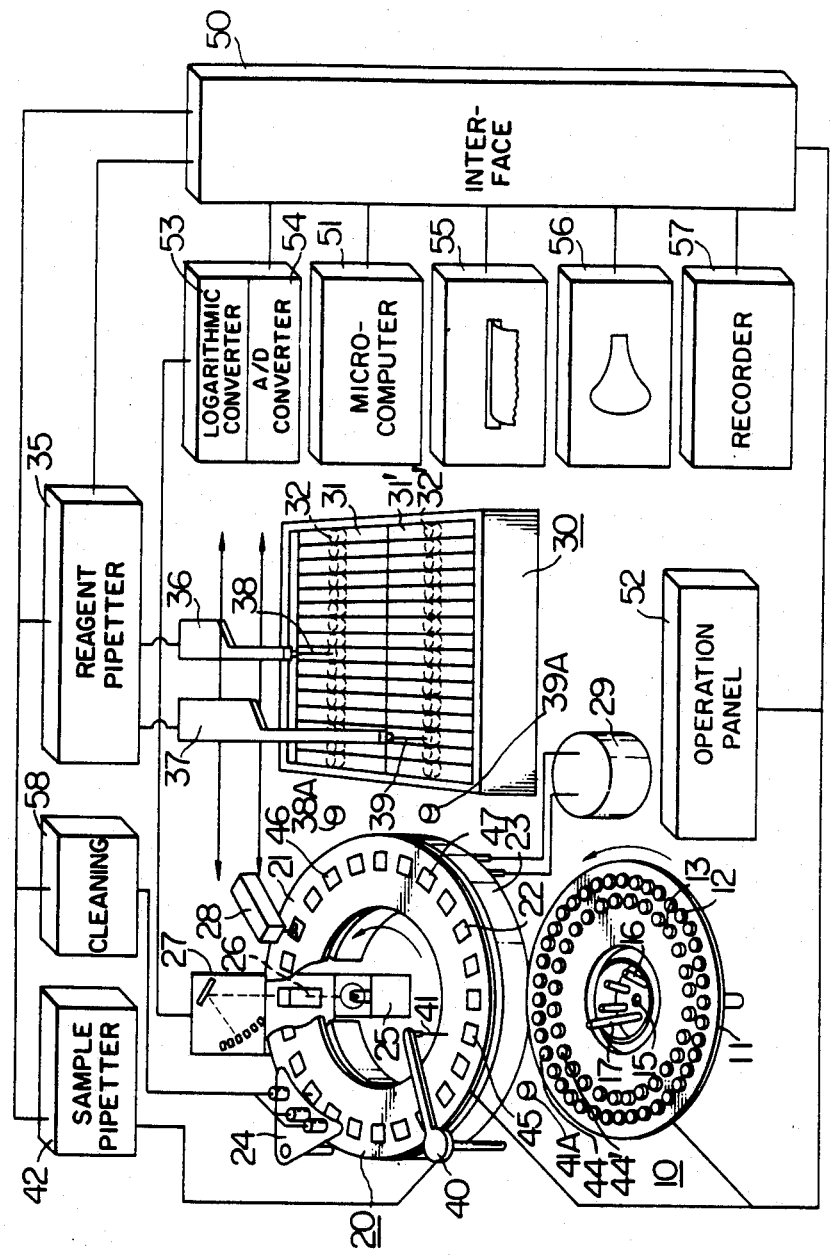

METHOD FOR ANALYZING LIQUID SAMPLE

BACKGROUND OF THE INVENTION

This invention relates to a method and an apparatus for analyzing a liquid sample, and more particularly to a method and an apparatus suitable for analysis of a desired component in a liquid sample by adding a reagent to a liquid sample, thereby initiating reaction, and measuring the rate of reaction.

According to the conventional method and apparatus for analyzing a liquid sample by measuring the rate of the reaction, the physical quantity of reacting mixture is measured only after all the reagent has been added to a sample. In the measurement of the rate of reaction, a change in physical quantity per unit time is measured, but in the case of a sample with a very high activity, the reaction proceeds at a very high rate, so that there may be no more substrate as a reactant at the timing of actual measurement and thus there is no more change in physical quantity. That is, an analysis value corresponding to that of a sample with a low activity is obtained.

Thus, in the measurement of the rate of reaction an effective limit level is set for measuring the physical quantity, so that an alarm flag can be displayed to indicate that the analysis of the liquid sample is no more effective, as soon as the physical quantity becomes less than the effective limit level if a reactant in the reaction is taken into account (substrate basis) or as soon as the physical quantity becomes more than the effective limit level if a product in the reaction is taken into account (product basis). However, the conventional method and apparatus have problems in complete functioning of the alarm system.

According to the conventional method and apparatus, the measurement is carried out only after all the reagent has been added to a liquid sample to initiate reaction, and thus the effective limit level is set equally for all the samples. Thus, there is such a problem that no alarm flag is displayed when a sample with an unexpectedly large change in the physical quantity is involved. For example, analysis of glutamate-oxalacetate transminase (GOT) in serum, which is widely carried out in hospital laboratories, is carried out according to the following reactions (1) and (2):

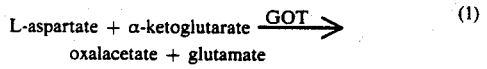
(1)

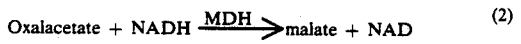
(2)

When an absorbance is measured at the wave length of 340 nm, a change in NADH can be traced, and consequently, the rate of reaction (1) by GOT can be determined in conjugation with reaction (2), wherein MDH stands for malate dehydrogenase, NADH for reduced nicotinamide adenine dinucleotide, and NDA for nocotinamide adenine dinucleotide.

Analytical items usually inspected in hospitals by measuring changes in NADH at the wave length of 340 nm include amylase, creatine phosphokinase, glucose, glutamate-pyruvate transminase (GPT), β-hydroxybutyrate dehydrogenase, lactate dehydrogenase (LDH), triglyceride, urea nitrogen, etc. However, absorbance at the wave length of 340 nm of serum as samples for analyzing these analytical items in hospital laboratories has some distribution. In FIG. 1, distribution of absorbance of 13-fold diluted serum samples of 200 patients in a hospital is shown. As is seen therefrom, the absorbance at the wave length of 340 nm has a large deviation depending upon the individual patients. Thus, the conventional method and apparatus based on the effective limit level being set by disregarding such a large deviation in the absorbance of serum have such a disadvantage that the alarm flag sometimes fails to function.

SUMMARY OF THE INVENTION

An object of the present invention is to prevent incorrect measurement of a liquid sample with a high activity as an analysis value of low activity due to shortage of a substrate at the timing of measurement.

Another object of the present invention is to analyze a liquid sample with high exactness in a maximum available range.

The object of the present invention is attained by measuring the physical quantity of the individual liquid sample before the initiation of reaction, setting an effective limit level for the individual liquid sample, adding a reagent to the liquid sample to initiate reaction, measuring physical quantities of the resulting liquid mixture in a plurality of repetitions from time to time before the effective limit level is reached, and automatically computing the analysis value of desired analytical item from the physical quantities thus obtained. That is, when an enzyme activity of a sample is so high that the amount of a substrate added to the sample becomes short, a low reaction rate is obtained, and such an incorrect analytical result as if the sample had a low enzyme activity may be obtained, but in the present invention, no such incorrect analytical result will be accepted at all.

The present invention is based on the finding that the physical quantity of a reacting liquid mixture of liquid sample and reagent is the sum total of a physical quantity due to the reagent and a physical quantity due to the sample, and the physical quantity due to the reagent depends upon the composition of the reagent. So far as a reagent of constant composition is used, the physical quantity due to such reagent has a constant value, whereas that due to a sample is variable, and has a value depending upon the composition of the individual sample.

The present invention provides a method for analyzing a liquid sample by adding a reagent to a liquid sample, thereby initiating reaction, and measuring a rate of reaction, thereby quantitatively determining an analytical item being contained in the sample and taking part in the reaction, which comprises:

(1) a step of measuring a physical quantity of the liquid sample,
(2) a step of setting an effective limit level for the liquid sample according to the physical quantity of the liquid sample,
(3) a step of adding a reagent to the liquid sample and measuring a physical quantity of the resulting liquid mixture, and
(4) a step of computing the analysis value of desired analytical item of the liquid sample from the physical quantities so far measured before the effective limit level is reached.

The present invention also provides a method for analyzing a liquid sample by rate analysis, which comprises a step of mixing a liquid sample with a first reagent, a step of positioning the resulting liquid sample to a first location of measuring a physical quantity of the liquid mixture, a step of first measurement of measuring the physical quantity of the liquid mixture positioned at the first location, a step of mixing the liquid mixture with a second reagent capable of initiating reaction for quantitative determination of desired analytical item, a step of positioning the resulting reaction-initiated liquid mixture to a second position of measuring a physical quantity of the liquid mixture, a step of second measurement of measuring the physical quantity of the liquid mixture positioned at the second location in a plurality of repetitions, thereby determining the rate of reaction initiated by the second reagent, a step of determining an effective limit level according to the physical quantity obtained in the step of first measurement, a step of discarding the physical quantities beyond the effective limit level from those measured in the step of second measurement, and a step of computing the analysis value of desired analytical item according to the remaining physical quantities of the step of second measurement so far obtained before the effective limit level is reached.

The present invention further provides an apparatus for analyzing a liquid sample by adding a reagent to a liquid sample, thereby effecting reaction, and measuring a rate of reaction, thereby quantitatively determining an analytical item being contained in the sample and taking part in the reaction, which comprises:

(1) a means of measuring a physical quantity of the liquid sample,
(2) a means of adding a reagent to the liquid sample and measuring a physical quantity of the resulting liquid mixture,
(3) a means of setting an effective limit level for the liquid sample according to the physical quantity of the liquid sample, and
(4) a means of computing the analysis value of desired analytical item of the liquid sample from the physical quantities so far measured before the effective limit level is reached.

The present invention still further provides an apparatus for analyzing a liquid sample by rate analysis, which comprises a means of effecting first timing and second timing for measuring a physical quantity of the liquid sample in sequence and positioning the liquid sample at the first timing and the second timing, a means of adding a first reagent to the liquid sample, thereby determining the state of the liquid sample before the liquid sample is positioned at a location of measuring the physical quantity for the first timing, a means of adding a second reagent to the liquid sample capable of reacting with a given component in the liquid sample after the first timing but before the second timing, a means of computing an effective limit level according to the physical quantity measured at the first timing, discarding the physical quantities beyond the effective limit level from those measured at the second timing, and computing the analysis value of desired analytical item according to the remaining physical quantities, and a means of displaying the analytical value by a signal processing means.

The physical quantity to be measured according to the present invention is a light intensity, which includes those based on absorbance, fluorescence, light scattering, luminescense, such as bioluminescence, or chemiluminescence, and is measured by a spectrophotometer, fluorophotometer, etc. The effective limit level is a light intensity level such as a light absorbance at which a correct measurement can be no more obtained due to the shortage of the substrate.

In the present invention, the effective limit level is set as a lower limit level, if the relevant reaction is handled on a substrate basis, or as an upper limit level, if the relevant reaction is handled on a product basis. That is, the analytical items can be grouped as follows, on the difference between the substrate basis and the product basis:

| Substrate basis | Product basis |
| --- | --- |
| (lower effective limit level to be set) | (upper effective limit level to be set) |
| GOT, GPT, LDH, Creatine phosphokinase, and triglyceride. | Glucose, urea nitrogen LDH, amylase, and alkaline phosphate |

To adjust the timing of initiating reaction, the reagent can be added to the liquid sample in sequence, and a plurality of analytical items can be measured one after another. The liquid reacting mixture can be measured in a plurality of repetitions by means of a turn-table.

BRIEF DESCRIPTION OF THE DRAWINGS

FIG. 2 is a schematic view of an apparatus for analyzing a liquid sample to be used in the present invention.

Figure 1:
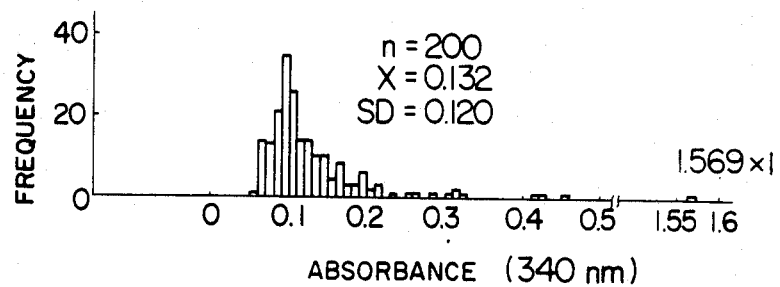
FIG. 1 is a diagram showing a distribution of absorbance of human serum.

The present invention will be described in detail below, referring to embodiments and drawings.

PREFERRED EMBODIMENTS OF THE INVENTION

General construction of an automatic analytical instrument according to an embodiment of the present invention is schematically shown in FIG. 2. In FIG. 2, the analytical instrument may be divided functionally into a sampling system, a reaction system, a reagent storage section, a reagent distributor section and a signal processing/control section.

First, the sampling system will be described. The sampling system includes sampler section 10 and sampling mechanism 40. Sampler section 10 has sample table 11 as a turn table, ion analyzing tank 15 and drive section for rotating sample table 11 and ion analyzing tank 15. Sample table 11 includes ordinary sample case array 12 loaded with samples to be analyzed in a plurality of holes on the outer periphery thereof, and special sample case array 13 loaded with emergency samples and reference samples in a plurality of holes on the inner periphery thereof. These sample cases are adapted to be transferred to sample suction positions 44 and 44' by rotation of table 11 as required. Ion analyzing tank 15 is arranged rotatably inside of sample table 11. A plurality of ion selecting electrodes 16 for sodium, potassium and chlorine ions and reference electrode 17 are extended within tank 15. These electrodes are adapted to be immersed in a diluent solution when the sample sampled from the sample cases by a sampling mechanism not shown is transferred into analyzing tank 15 and diluted by the diluent solution.

Sampling mechanism 40 includes a rotary arm holding sample processing tube 41, a vertical drive mechanism for the rotary arm, and sample pipetter 42 for moving sample processing tube 41 between sample suction positions 44 and 44' and sample discharge position 45 at each of which specimen processing tube 41 is adapted to be driven vertically.

Sample processing tube 41 of sampling mechanism 40 is cleaned by cleaning section 41A before suction of the sample. Cleaning section 41A is provided midway in the path of movement of sample processing tube 41.

Next, the reaction system will be explained. Reaction section 20 includes temperature-maintained annular path 23 and reaction table 21 arranged thereon. Reaction table 21 is disposed as high as sample table 11. Temperature-maintained path 23 includes a temperature-maintained tank and receives a temperature-maintained liquid from temperature-maintained water supply section 29. The temperature of the water in temperature-maintained water supply section 29 is variable over the range between, say, 25° C. and 37° C. Reaction table 21 has a multiplicity of holes each loaded with reaction case 22 of a rectangular transparent cell, thus forming an array of reaction cases. The lower part of the reaction cases is immersed in the temperature-maintained liquid.

Light source 25 is provided inside of reaction table 21 rotated either continuously or intermittently by a drive mechanism not shown. Light fluxes 26 from light source 25 are led to photometer 27 through reaction cases 23 in temperature-maintained path 23, and dispersed by the diffraction grating in photometer 27, so that a light ray of specified wavelength is taken out by way of a photosensor. The contents of reaction cases 22 are agitated by agitator 28.

Cleaning machine 24 having a plurality of pure water discharge tubes and liquid suction tubes is arranged over the reaction case array. When reaction table 21 is stationary, these tubes are inserted into the reaction cases thereby to clean the reaction cases. Cleaning machine 24 has cleaning syringe means 58 for performing a cleaning cycle including the suction of the liquid by the liquid suction tube, the pure water discharge by the pure water discharge tube and the pure water suction by the liquid suction tube. This cleaning cycle is repeated three times for each reaction case.

The reagent storage section will be described. Reagent storage section 30 is disposed in proximity to reaction section 20 in such a manner that the height of reagent cases 31 and 31' is substantially the same as that of reaction table 21. Storage section 30 includes a refrigerator which contains two lines of series arranged reagent cases 31 and 31' in the form of reactangular parallelepiped. Each of cases 31 and 31' is prepared according to the analysis item and has openings 32 and 32'.

Now, the reagent distribution system will be described. Reagent pipetter 35 has reagent pipetting sections 36 and 37 transferred along a rail not shown. Reagent absorbing-discharging tubes 38 and 39 are mounted on pipetting sections 36 and 37. Reagent absorbing-discharging tubes 38 and 39 are adapted to reciprocate independently of each other. Reagent absorbing-discharging tube 38 is moved along the line of openings 32 up to reagent discharge position 46. On the other hand, reagent absorbing-discharging tube 39 is adapted to move along the line of openings 32' up to reagent discharge position 47. The line of reagent cases 31 and that of cases 32' are arranged in parallel to each other, and so are the lines of openings 32 and 32'. Reagent storage tanks 31 and 31' are rectangular parallelepiped in form and therefore a multiplicity of them can be arranged in closely adjacent relation to each other. Reagent absorbing-discharging tubes 38 and 39 are stopped over an appropriate opening of reagent tanks 31 and 31' according to the analytical item involved, and moved down to take in and hold the reagent, followed by the upward movement thereby to discharge the reagent held into reaction case 22. Reagent absorbing discharging tubes 38 and 39 are cleaned at cleaning sections 38A and 39A respectively before suction of the reagent. Opening 32 of reagent case array 31, cleaning section 38A and reagent discharge position 46 of reaction table 21 are aligned in a straight line. Reagent absorbing-discharging tubes 38 and 39 have a reagent surface level sensor not shown, in response to the output of which the surface level of the reagent is detected. The operation of this sensor causes reagent absorbing-discharging tubes 38 and 39 to constantly take in a predetermined amount of reagent. Reagent pipetting sections 36 and 37 have a preheater not shown for heating the reagent up to a temperature proper for reaction while reagent absorbing-discharging tubes 38 and 39 moves to reagent discharge positions 46 and 47.

Finally, the signal processing/control system will be explained. Logarithmic converter 53 is for logarithmic conversion of a measurement signal according to the intensity of the transmitted light from photometer 27. The resulting conversion value is applied to the A/D converter 54 for conversion into a digital signal. Printer 55 is for printing the measurement result by analytical item of the reagent. Cathode ray tube 56 is for displaying the result of measurement and the conditions of analysis. Cassette tape recorder 57 is used for analysis with the cassette tape storing the conditions of analysis. After the cassette tape is read by cassette tape recorder 57, the reagent tank is replaced, thus automatically enabling the item of analysis to be changed. Operating panel 52 is used for entry of the analytical item and the conditions of analysis by item from outside by way of the item keys, profile keys and ten keys. Microcomputer 51 is in charge of general control of the apparatus. Microcomputer 51 is for controlling the sampling system, the reaction system, the reagent storage section and the reagent distribution system on the one hand, and for exchange of information with A/D converter 54, printer 55, cathode ray tube 56, cassette tape recorder 57 and operation panel 52 through interface circuit 50 on the other hand.

Sample table 11 carrying a sample to be analyzed is placed on sampler 10 and the start button of operation panel 52 is pressed down. Then the operation of the analytical instrument starts. Sample absorbing-discharging tube 41 of sampling mechanism 40 absorbs and holds the sample at sample suction position 44 or 44' and discharges the held sample at sample discharge point 45. The array of reaction cases 22 is transferred to cross light rays 26 and reaction table 21 makes one revolution plus one step so that the reaction case next to the one that has received the sample is positioned at sample discharge point 45. This sampling operation is continuously repeated. Sample table 11, after being sampled a number of times equal to the number of analytical items, makes a rotation by one step in preparation for the next sample analysis.

In this way, reaction table 21 makes one rotation and one step for each sampling process, while the reaction case that has accepted the sample for the first time reaches reagent discharge position 47. Reagent pipetting section 37 absorbs a reagent corresponding to the analytical item from reagent tank 31', and while holding the same, moves to reagent discharge point 47 where the reagent is discharged into the reaction case. The sample in the reaction case reacts and present a color when the reagent is added thereto.

After discharge of the reagent, reagent absorbing-discharging tube 39 of reagent pipetting section 37 is cleaned by cleaning section 39A in preparation for the next reagent discharge to the reaction case. When the first reaction case reaches reagent discharge point 46, reagent pipetting section 37 executes the reagent distribution if required according to the analytical item.

Reagent pipetting sections 36 and 37 are respectively hung from the rails and are capable of moving along the rails. These pipetting sections 36 and 37 are also capable of moving vertically together with the rails. Reagent absorbing-discharging tubes 38 and 39 may be stopped at openings 32 and 32' of each reagent tank if required. The operation of the drive section of pipetting sections 36 and 37 is controlled by microcomputer 51. The reagent corresponding to the analytical item of the sample that has reached discharge positions 46 and 47 is selected by reagent pipetting sections 36 and 37 so that absorbing-discharging tubes 38 and 39 provisionally stop over corresponding reagent tanks 31 and 31'. This is followed by the downward movement of pipetting sections 36 and 37 with the result that the operation of reagent pipetter 35 causes a predetermined amount of reagent to be absorbed and held by absorbing-discharging tubes 38 and 39. Then, pipetting sections 36 and 37 move upward, so that absorbing-discharging tubes 38 and 39 are horizontally moved to reagent discharge positions 46 and 47, and the reagent held in the absorbing-discharging tubes is discharged into the corresponding reaction case.

As reaction table 21 rotates each time of sampling operation, the sample in the reaction case crosses light rays 26 by the sampling operation, thus enabling the observations of the colored conditions. In other words, the optical characteristics of the same sample can be observed a plurality of times before the reaction case reaches the position of cleaning machine 24.

The wavelength required for the analytical item involved is selected by the wavelength selector circuit not shown from the light received at the photoelectric detector of photometer 27, so that the signal of a magnitude associated with the intensity of the transmitted light is introduced to logarithmic converter 53. Subsequently, the analog signal is converted into a digital signal at A/D converter 54, and through interface circuit 50, led to microcomputer 51, where the required calculations are made and the result thereof is stored in the memory. After completion of all the plurality of light measuring operations on the specified analytical item, the plurality of light measurement data are compared with each other and the required calculations are made thereby to print the analysis value as the analytical item involved on printer 55.

In this way, the measurement is completed when the reaction case containing the first sample has passed the position of the photometer. And when the reaction case reaches the cleaning position, it is cleaned by the cleaning machine 24 in preparation for the measurement of the next sample.

In the foregoing embodiment, analysis can be carried out by colorimetry or by measuring the rate of reaction. The operations of the apparatus for analysis are memorized in the cassette tape, and the change of analytical items can be carried out by reading the cassette tape and by consequent exchange of reagent cases, obviating cleaning of the line at the exchange of reagents. Furthermore, input of analytical items and their conditions can be carried out manually by means of cathode ray tube, items keys, profile keys and ten keys.

An example of analyzing glutanate-oxalacetate transminase (GOT) in serum according to the present invention will be described below.

Figure 3:
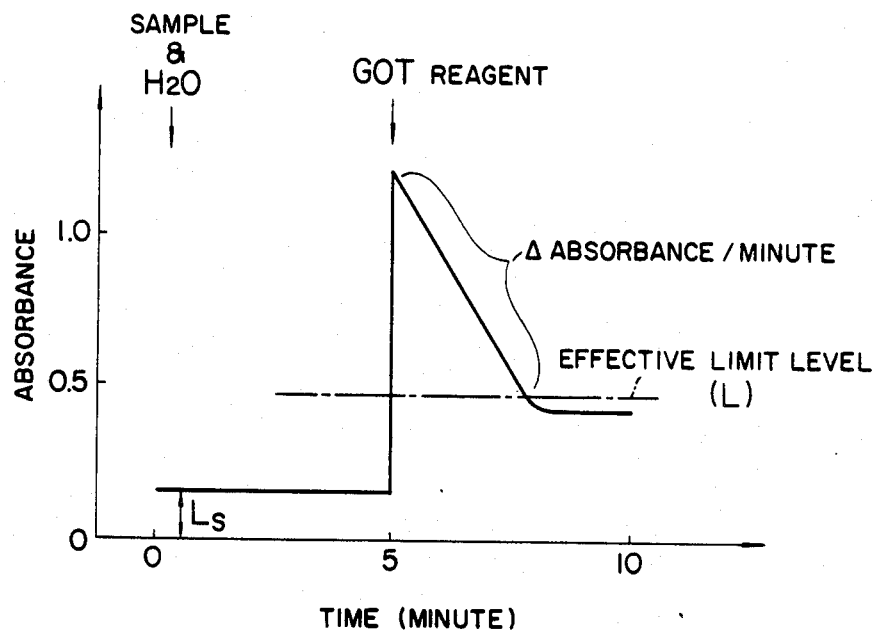
FIG. 3 is a diagram showing relations between the timing of reagent to a liquid sample and progress of reaction.

In FIG. 3, relations between the absorbance of a liquid sample and time in the analysis of GOT are shown, where 20 μl or a sample and 300 μl of H₂O are mixed at time "0", and 20 seconds thereafter the absorbance of the liquid sample is measured to obtain an absorbance level ($L_s$) of the liquid sample. 5 minutes thereafter, 200 μl of a reagent having the following composition for measuring GOT is added to the liquid sample to initiate reaction.

| Composition of reagent | |
|---|---|
| L-aspartate | 600 mM/l |
| α-ketoglutamate | 30 mM/l |
| NADH | 0.45 mM/l |
| phosphate buffer (pH 7.4) | 200 mM/l |
| MDH | 1 IU/ml |

The effective limit level (L) is automatically set from the absorbance level ($L_s$) of the liquid sample, and an absorbance level ($L_r$) of the reagent predetermined by the composition of the reagent according to the following equation:

$$L = L_r + \frac{SV + R_1}{SV + R_1 + R_2} \times L_s$$

wherein
SV: the volume of liquid sample, i.e. 20 μl
$R_1$: the volume of H₂O, i.e. 300 μl
$R_2$: the volume of GOT reagent, i.e. 200 μl The progress of reaction is traced by reading absorbance at 340 nm until the read value comes down to the established effective limit level for the respective sample, or for a definite time, for example, for 5 minutes, if the read value does not reach the established effective limit level for the respective sample, to determine the rate of reaction (Δ absorbance/minute), and the analysis value, for example, activity or concentration, of the desired analytical item, that is, GOT, is derived from the thus obtained data according to the predetermined calculation formula, which is a calculation formula obtained from a formula of working curve obtained by the measurement of the standard liquid solution or from the definition of enzyme activity. Here, the reagent level (Lr) is an absorbance level originating from the reagent, and so long as the reagent once prepared is used, it is at a constant value. Usually, the reagent level (Lr) is measured when the reagent solution is prepared, and stored in the memory of a computer and served for calculation when required.

In the foregoing formula, the term $$\left( \frac{SV + R_1}{SV + R_1 + R_2} \times L_s \right)$$

is a variable originating from the sample, and the variable is called a correction level originating from the sample. Ls can be obtained from ($L_s = L_m - L_b$) as will be described later, and when $R_1$ is directed to water, $L_b = 0$, and the effective limit level (L) can be obtained.

Figure 4:
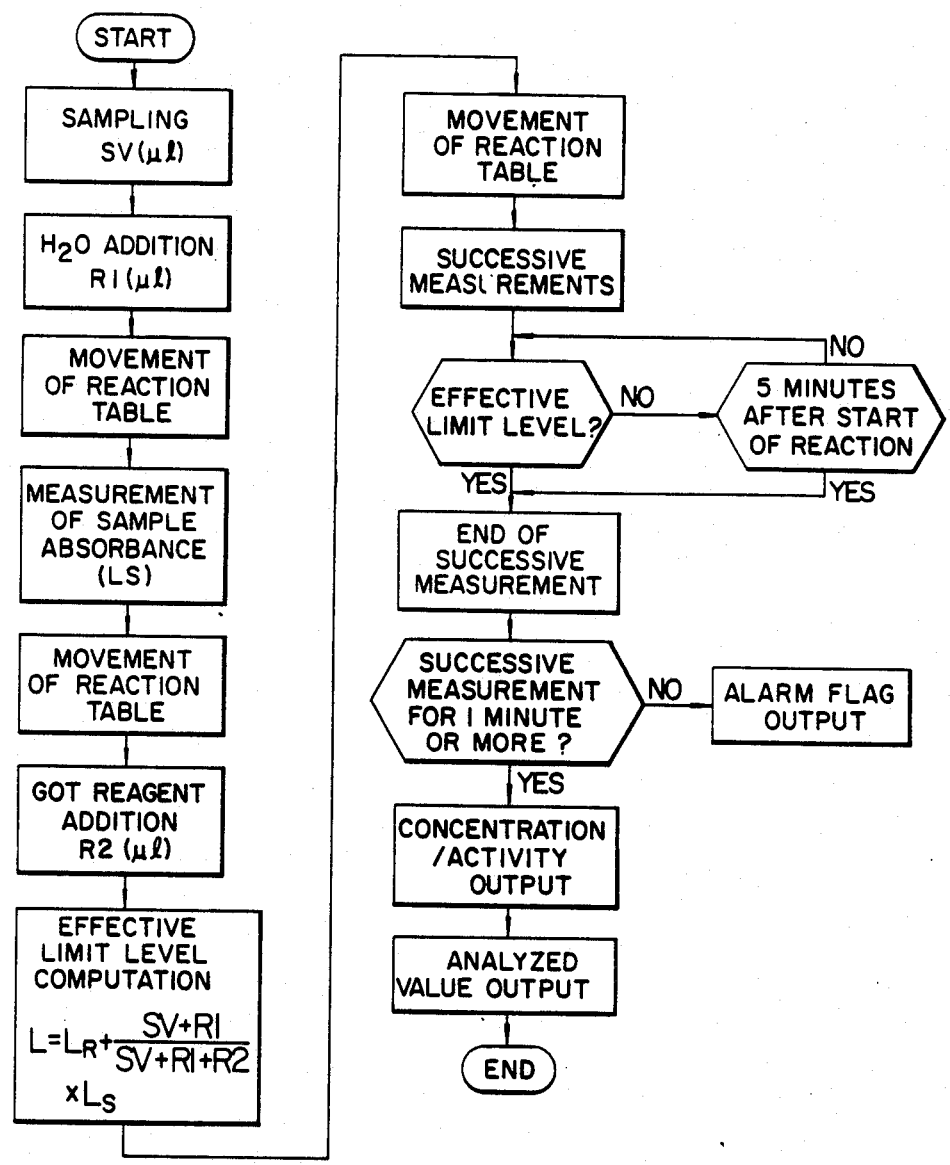
FIG. 4 is a flow chart showing operation according to one embodiment of the present invention.

FIG. 4 shows a flow chart for operations of the embodiment shown in FIG. 3. When the measurement reaches the effective limit level earlier, the measuring operation is discontinued and the measurement value is discarded, as is evident from FIG. 4.

The present invention is not limited to $H_2O$ as a liquid to be added to a liquid sample to determine the absorbance level ($L_s$) of the liquid sample, as shown in FIG. 3. So long as a liquid sample is in an amount large enough for the measurement of an analytical item, it is not necessary to add $H_2O$ to the liquid sample. In the embodiment according to FIG. 3, another component of the reagent taking part in the GOT reaction can be added to the liquid sample in place of $H_2O$. That is, a first reagent consisting of L-aspartate, MDH, NADH and phosphate buffer can be added to the liquid sample in place of $H_2O$, and 5 minutes thereafter α-ketoglutarate can be added thereto as a second reagent to initiate the GOT reaction. The absorbance level ($L_r$) based only on the α-ketoglutamate solution is stored in memory as an absorbance level of the second reagent. The first reagent cannot substantially initiate the quantitative reaction of an analytical item. In that case, the absorbance level ($L_s$) of the liquid sample is measured at first only for the first reagent ($L_b$), and memorized. Then, an absorbance level of a liquid mixture of a liquid sample and the first reagent ($L_m$) is measured for the individual sample, and $L_s$ can be obtained according to the following formula:

$$L_s = L_m - L_b$$

As described above, an exact effective limit level can be automatically set for the individual liquid sample according to the present invention, and an analysis value of desired analytical item can be obtained in the analysis by measuring the rate of reaction.

What is claimed is:

1. A method for analyzing a liquid sample by rate analysis quantitatively determining an analytical item contained in the sample, which comprises a step of adding a reagent to a sample to obtain a resultant liquid sample, a step of positioning the resultant liquid sample to a first location of measuring a physical quantity of the liquid sample, a step of effecting a first measurement of the light intensity of the liquid sample positioned at the first location, a step of mixing the liquid sample with a second reagent capable of initiating reaction for quantitative determination of desired analytical item, a step of positioning the resulting reaction-initiated liquid mixture to a second position of measuring the light intensity of the liquid mixture, a step of effecting second measurements of the light intensity of the liquid mixture positioned at the second location in a plurality of repetitions for a predetermined time, thereby determining the rate of reaction initiated by the second reagent, a step of calculating an absorbance level value ($L_s$) based on the value of the first measurement ($L_m$) and a absorbance level value ($L_b$) based only on the first reagent determined in advance, a step of calculating an effective limit level (L) corresponding to the absorbance level value ($L_s$) and an absorbance level value ($L_r$) based only on the second reagent determined in advance, a step of discarding any second measurement values obtained after a set effective limit level is reached within said predetermined time, and a step of computing an analysis value of said desired analytical item according to light intensity values of the second measurement step obtained before the effective limit level value is reached.

2. The method according to claim 1, wherein the physical quantities in the steps of first measurement and second measurements are measured by an identical means for measuring light intensities.

3. A method for analyzing a liquid sample for quantitively determining an analytical item contained in the sample which comprises:
   (1) a step of measuring a light intensity of the liquid sample before the liquid sample is allowed to undergo reaction for determining an absorbance level value (L),
   (2) a step of adding reagent to the liquid sample, thereby initiating the reaction for determining the analytical item, and then in a plurality of repetitions measuring light intensity of the resulting liquid mixture,
   (3) a step of calculating an effective limit level (L) from absorbance level value ($L_s$) obtained in the measuring step (1) and absorbance level value ($L_r$) based on the reagent, and
   (4) a step of computing an analysis value of said desired analytical item during a predetermined time interval only until measurement values in step (2) reach the effective limit level.

4. The method according to claim 3, wherein the steps (1) and (2) are carried out by an identical means for measuring light intensities.

5. The method according to claim 3, wherein the step (2) is carried out in a plurality of repetitions from time to time by means of a turn-table.

6. The method according to claim 3, wherein the light intensity is measured by absorbance, fluorescence, light scattering or luminescence.

7. The method according to claim 3, wherein the reagent is added to the sample in sequence, thereby adjusting the timing of initiating the reaction.

8. The method according to claim 3, wherein a plurality of analytical items are measured one after another.

9. The method according to claim 3, wherein the effective limit level (L) is automatically set from the absorbance level ($L_S$) of the liquid sample and an absorbance level ($L_R$) of the reagent predetermined by composition of the reagent in accordance with the equation:

$$L = L_R + \frac{SV + R_1}{SV + R_1 + R_2} \times L_s$$

where SV is the volume of the liquid sample, $R_1$ is the volume of a liquid which can be added to the liquid sample to determine the absorbance level (Ls) of the liquid sample when the amount of liquid sample is not sufficiently large enough for measurement of the analytical item, and $R_2$ is the volume of a reagent.

* * * * *